United States Patent [19]

Huebsch

[11] Patent Number: 5,064,426
[45] Date of Patent: Nov. 12, 1991

[54] APPARATUS FOR REMOVAL OF BONE CEMENT

[76] Inventor: Donald L. Huebsch, 3716 Prestwick Dr., Los Angeles, Calif. 90027

[21] Appl. No.: 319,949

[22] Filed: Mar. 7, 1989

Related U.S. Application Data

[60] Division of Ser. No. 232,506, Aug. 15, 1988, Pat. No. 4,873,969, which is a continuation-in-part of Ser. No. 131,830, Dec. 11, 1987, abandoned.

[51] Int. Cl.$^5$ .......................... A61F 7/00; A61B 17/00
[52] U.S. Cl. .......................................... 606/92; 606/29; 606/30
[58] Field of Search ............ 128/92 VP, 92 V, 92 VJ, 128/303.1, 303.14, 92 VM, 303 B, 92 R; 606/92-94, 53

[56] References Cited

U.S. PATENT DOCUMENTS

| | | | |
|---|---|---|---|
| 1,234,570 | 7/1917 | Rink | 128/303.1 |
| 1,355,932 | 10/1920 | Walter | 128/303.1 |
| 2,095,678 | 10/1937 | Slutz | 128/303.1 |
| 3,412,733 | 11/1968 | Ross | 128/92 VJ |
| 3,526,750 | 9/1970 | Siegel | 128/303.14 |
| 3,558,854 | 1/1971 | Siegel | 128/303.14 |
| 3,919,522 | 11/1925 | Wahl | 128/303.14 |
| 4,124,026 | 11/1978 | Berner | 128/92 V |
| 4,248,232 | 2/1981 | Engelbrecht | 128/92 V |
| 4,265,231 | 5/1981 | Scheller | 128/92 V |
| 4,293,962 | 10/1981 | Fuson | 128/92 V |
| 4,593,685 | 6/1986 | McKay | 128/92 R |
| 4,632,100 | 12/1986 | Somers | 128/92 V |
| 4,685,458 | 8/1987 | Leckrone | 128/303.1 |
| 4,686,973 | 8/1987 | Frisch | 128/92 R |
| 4,696,292 | 9/1987 | Heiple | 128/92 V |
| 4,702,236 | 10/1987 | Tarabichy | 128/92 VP |

Primary Examiner—Robert A. Hafer
Assistant Examiner—Michael Brown

[57] ABSTRACT

Bone cement is removed from a bone cavity, such as the intramedullary canal, during a prosthetic revision. The bond cement is pre-molded by a thermal chisel which includes a shaft for extending into the bone cavity, a plasticizer chisel on a working end of the shaft, and a heat element carried by the shaft for heating the chisel to a temperature within a range of temperatures sufficient to plasticize the bone cement. This deforms and weakens the bone cement upon direct non-impact type contact between the heated tip of the chisel and the cement. The cement is removed by pre-molding it with the heated working end of the thermal chisel, preferably by molding a distally located circumferential furrow in the bone cement and then molding circumferentially spaced apart longitudinal furrows from the circumferential groove to the proximal end of the bone cement. Upon rehardening of the bone cement, these thermally molded furrows form weakened areas within the bone cement so that the regions of bone cement between the weakened areas can be removed by an impact type chisel. Preferably, each section of bone cement is removed intact by impact force applied to a molded step groove in a proximal end surface of the section. Removal of the bone cement in sections by these procedures avoids harmful heat transfer to the bone wall.

16 Claims, 3 Drawing Sheets

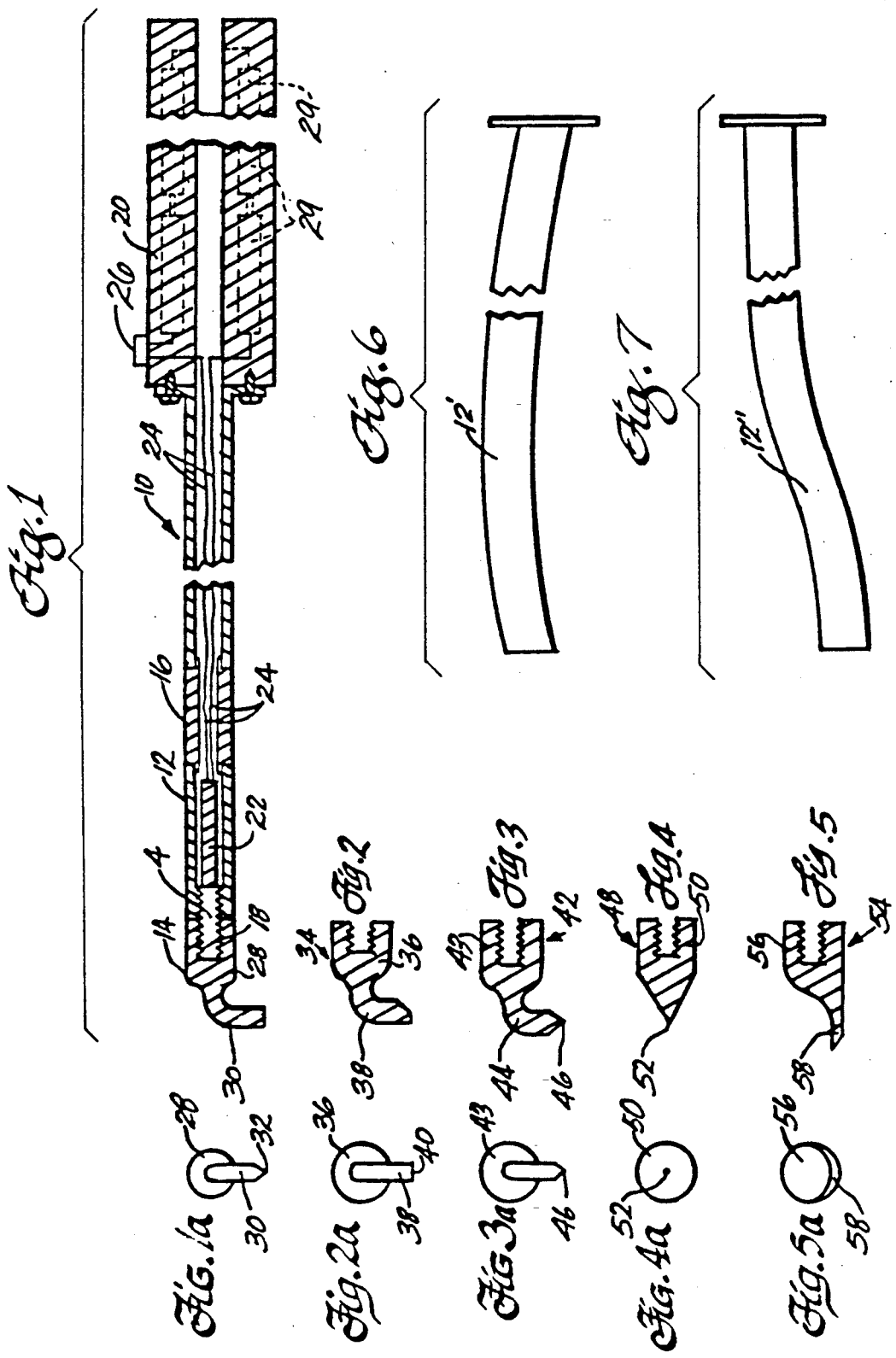

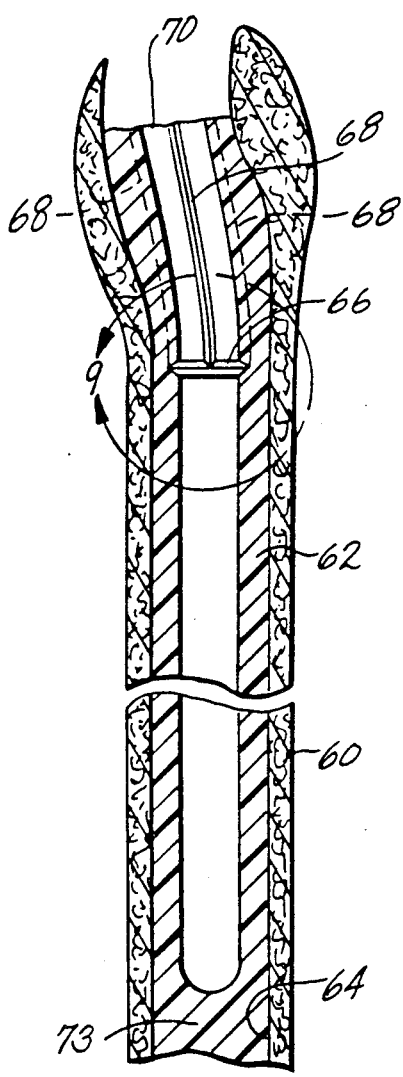
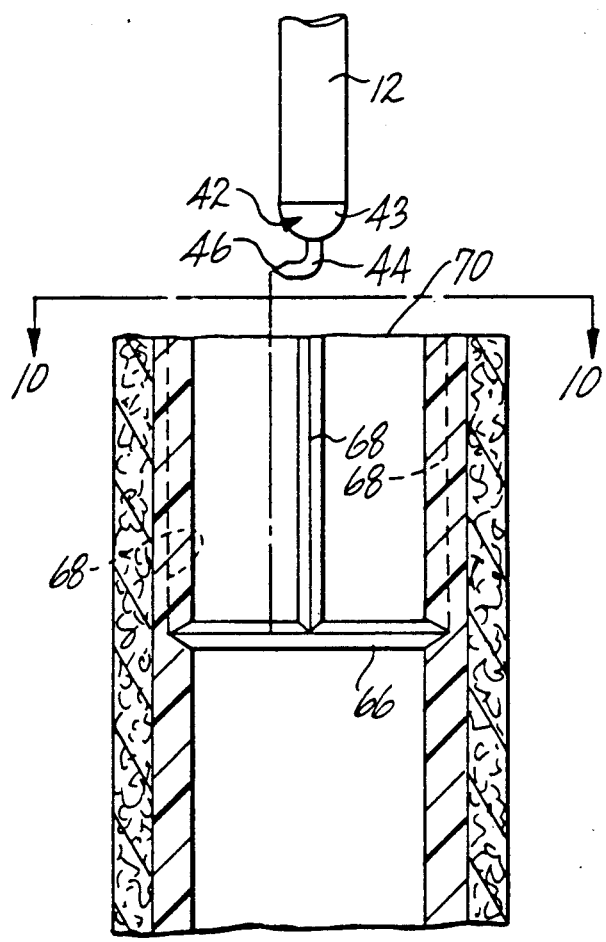
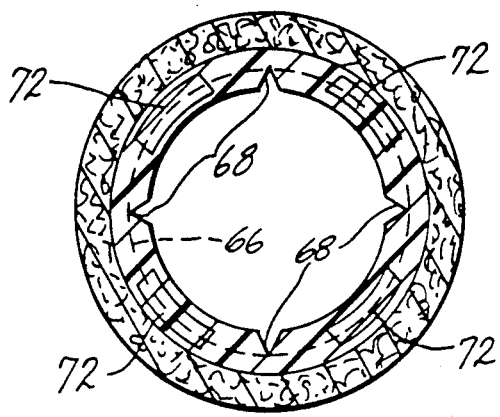

APPARATUS FOR REMOVAL OF BONE CEMENT

CROSS-REFERENCE TO RELATED APPLICATION

This is a division of application Ser. No. 232,506 filed Aug. 15, 1988, now U.S. Pat. No. 4,873,969, which is a continuation-in-part of application Ser. No. 131,830, filed Dec. 11, 1987, now abandoned.

FIELD OF THE INVENTION

This invention relates to techniques for removal of bone cement during a prosthetic revision, for example, and more particularly, to a method and apparatus for removing bone cement from a bone cavity without damaging the bone.

BACKGROUND OF THE INVENTION

It is common for the femoral component of a cement hip prosthesis to require revision after a number of years in use. The revision involves removal of the femoral stem portion of the endoprosthesis anchored in the intramedullary canal. Removal of the endoprosthesis does not itself require a great deal of surgical time. The bone cement left, however, does require a great deal of surgical time to remove.

Numerous impact-type chisels and high and low speed drills have been used in various combinations for removing bone cement. A problem facing the surgeon is the lack of control over the impact chisel or drill, since they can drift from origin during use. As a result, the device will occasionally penetrate the femur wall.

Bone cement generally has a hard smooth surface which makes it difficult, if not impossible, to get a good bite with a chisel or drill. This, coupled with the lengthy surgical time, leaves room for improvement.

Bone cement is widely accepted as the leading anchoring medium for the femoral component to the medullary canal wall. In addition, it has been found with great success that once bone cement has been removed, the cancellous bone will grow into a cementless femur stem.

It is imperative that the bone be protected against unnecessary exposure to extreme heat. When bone cement is used to anchor the prothesis in a bone cavity, the bone cement transmits a considerable amount of heat to the bone during its exothermic curing process. These temperatures can approach 80° C. (180° F.) over a period of about four minutes. Normally, this does not damage the bone.

It has been proposed to remove bone cement from the femoral medullary canal during a hip revision using a thermal chisel. Such techniques are described, for example, in U.S. Pat. No. 4,702,236 to Tarabichy, et al. These techniques comprise use of instruments with heated working ends of various shapes heated to a temperature exceeding the melting point of the bone cement. According to Tarabichy, et al., the heated instruments are used to scoop out the cement by penetrating the instrument into the cement by melting the cement, until penetration is arrested by the wall of the bone. Substantially all of the cement is removed from the bone cavity by continued use of these heated instruments until sufficient bone cement is removed for reanchoring the removed prosthesis.

Tarabichy, et al., disclose that the thermal chisel is heated to a temperature above the melting point of the cement, i.e., about 150° to 200° C., in order to soften the cement to the point where it can be removed by the heated instrument.

However, it has been found that the tip of such a heated instrument should operate at a temperature in the range of about 400° C. to about 450° C., in order to plasticize the bone cement, in a practical length of time, for reasonably fast and easy removal. These temperatures are far in excess of temperatures that, by direct contact with the bone wall, can permanently damage the bone and its adjacent tissue.

Certain concerns have been raised as to the thermal effect of these prolonged temperatures on survival of the bone, particularly if substantial contact occurs between the heated working end of the instrument and the bone wall.

The amount of heat transfer to the bone wall is directly proportional to the area, temperature and time of contact of the heat source, i.e., the surface area of the heated tip of the instrument which may contact the bone wall. Since the scoop-type heated instruments disclosed in the Tarabichy et al patent may have a rather large surface area, a potentially damaging amount of heat can be transferred to the bone wall when removing the bone cement. This problem is particularly critical if contact with the bone wall is used as the means for arresting penetration of the heated tip of the instrument, and if the instrument is heated to the higher temperatures which are more effective in removing the cement.

Excessive heat is far more damaging to the bone and adjacent tissue then accidental penetration of the bone with impact chisels of the type used in the prior art for removal of bone cement. Although the bone cement itself provides some protection for the bone during removal of the bone cement, the large area of heat contact between heated instruments and the bone wall can transmit damaging heat to the bone, not only through contact with the heated working end of the instrument, but also with the shaft of the instrument.

Additionally, concerns have been raised about the use of instruments, within the human body, operating at the conventional deadly 120 volts.

The present invention provides a method and apparatus for removing bone cement from a bone cavity by avoiding damaging heat transfer to the wall of the bone when the bone cement is being removed while utilizing voltages of less than 24 volts isolated from the normal utility 120 volt outlet source.

SUMMARY OF THE INVENTION

Briefly, one embodiment of this invention provides a method for removing a thermoplastic bone cement from a bone cavity by a surgical instrument having an electrical (less than 24 volts) heated working end used to mold in the bone cement into sections. Upon rehardening of the bone cement, the molded areas become weakened structurally. A surgical impact type chisel is then used for removing sections of bone cement between the weakened areas by direct impacting of the chisel on each section of bone cement. The process is repeated until all bone cement is removed from the bone cavity.

In one form of the invention, the method includes using a heated instrument having a working end which is pointed and mounted normal to the axis of the instrument, in which the tip, upon reaching a temperature sufficient to plasticize the bone cement, is used to mold a circumferential furrow in a distal region of the cement. A plurality of circumferentially spaced apart longitudinal furrows are molded from the distal circumferential furrow to the proximal end of the bone cement. A molded step groove is then molded at the proximal end of a region of bone cement between adjacent longitudinal furrows. Each section of bone cement is then removed by placing an impact chisel in the proximal molded groove and impacting the chisel. The molded groove provides the impact chisel with a good bite and prevents it from drifting during impacting. This process is repeated until all of the bone cement is removed from the bone cavity.

The furrows are formed in the bone cement to mold indentations in the bone cement (without removing the bone cement) sufficiently to weaken the bone cement at circumferentially spaced apart regions, upon rehardening of the cement. Impact by the impact chisel can remove large intact sections of the bone cement from the bone cavity between the weakened areas produced by the thermal molding steps.

An embodiment of the invention provides a surgical instrument for removing bone cement from a bone cavity without transfer of damaging heat to the bone wall. Damaging heat transfer to the bone wall can be avoided even though the tip of the instrument is heated to temperatures in the range of 400° to 450° C. The instrument includes an elongated shaft for extending into the cavity, a plasticizer chisel mounted on the working end of the shaft. An electrical heating element carried by the shaft heats the chisel to a temperature within a range of temperatures sufficient to transfer heat to plasticize the bone cement. Use of the chisel deforms and weakens the bone cement upon direct non-impact type contact between the heated chisel tip and the bone cement. The instrument includes edge tangential point protection rings projecting outwardly from the shaft of the instrument adjacent the heated tip to protect the bone from unnecessary heat transfer during accidental contact of the thermal chisel with the bone wall. If the thermal chisel comes into contact with the bone wall, only point tangential contact is made with the bone, providing a minimal area of contact and greatly reduced heat transfer to the bone wall.

The instrument utilizes a heating element operating in the range of less than 24 volts provided from a battery source contained within the instrument or externally of the instrument. This provides a power source preferably not connected to the normal utility 120 volt outlet wherein voltage reduction devices may cause exposure of potentially dangerous voltages to the patient and surgeon.

Thus, the invention provides the following improvements:
(1) Controlled thermal means to mold the bone cement to weaken and sectionalize it prior to use of impact chisels to remove the bone cement.
(2) Controlled removal of the bone cement avoiding harmful heat transfer to the bone wall.
(3) Instruments which safely remove the bone cement without damaging penetration of the or contact with the bone wall.
(4) Reduced surgical time required to remove the bone cement.
(5) Electrical heating element powered by less than 24 volt batteries isolating the instrument from dangerous standard 120 volt voltages.

These and other aspects of the invention will be more fully understood by referring to the following detailed description and the accompanying drawings.

BRIEF DESCRIPTION OF THE DRAWINGS

FIG. 1 is a fragmentary, longitudinal cross-sectional view illustrating a surgical instrument which may be used in a method for removing bone cement according to principles of this invention.

FIG. 1a is an end view of a thermal chisel tip taken on line 1a—1a of FIG. 1.

FIG. 2 is a cross-sectional view of an alternate embodiment of a thermal chisel tip.

FIG. 2a is an end elevation view taken on line 2a—2a of FIG. 2.

FIG. 3 is an alternate embodiment of a thermal chisel tip.

FIG. 3a is an end elevation view taken on line 3a—3a of FIG. 3.

FIG. 4 is an alternate embodiment of a thermal chisel tip.

FIG. 4a is an end elevation view taken on line 4a—4a of FIG. 4.

FIG. 5 is an alternate embodiment of a thermal chisel tip.

FIG. 5a is an end elevation view taken on line 5a—5a of FIG. 5.

FIG. 6 is a fragmentary side elevation view illustrating the shape of a shaft of the surgical instrument to facilitate use of a specific thermal chisel tip.

FIG. 7 is a side elevation view illustrating a further alternate shape of the shaft of the surgical instrument to facilitate use of another thermal chisel tip.

FIG. 8 is a semi-schematic, longitudinal cross-sectional view showing a method for removing bone cement from a bone cavity according to principles of this invention.

FIG. 9 is an enlarged fragmentary semi-schematic cross-sectional view taken within the circle 9 of FIG. 8.

FIG. 10 is a semi-schematic elevational view taken on line 10—10 of FIG. 9.

DETAILED DESCRIPTION

Figure 11A:
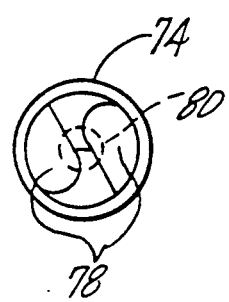
FIG. 11a is an end view taken on line 11a—11a of FIG. 11.

FIG. 1 illustrates a surgical instrument comprising a thermal chisel 10 for use in removing bone cement from a bone cavity. The instrument is used in a method for pre-molding bone cement to weaken and sectionalize it prior to removing it with an impact device described in more detail below. The instrument 10 includes an elongated tubular shaft 12 which, in the embodiment of FIG. 1, is a straight tubular shaft. Alternatively, the tubular shaft can be in different shapes, such as the curved shape of the alternative shaft 12' shown in FIG. 6, or the composite straight and curved shaft 12" shown in FIG. 7. The shaft also can either be made from a rigid material, or a semi-rigid material having the ability to be bend laterally to conform to a desired shape in order to accommodate insertion of the instrument into a bone cavity of comparable shape. The shaft portion 12 of the instrument 10 also is of sufficient length to extend the instrument far enough into the bone cavity so that bone cement near the bottom of the bone cavity can be reached by the instrument.

The instrument 10 further includes a thermal chisel 14 secured to the working end of the shaft. The chisel is preferably fastened by a threaded connection which includes an externally threaded metal stud 4 mounted in the end of the shaft and projecting forward for connection to an internally threaded bore 18 inside the chisel 14. The chisel is removable from the instrument so that chisels of various configurations, described below, can be used during the process of molding the bone cement. A heat barrier 16 preferably made of Corning Glass Works (Corning, N.Y.) Macor is cemented with a thermally resistant cement within the shaft 12 to prevent heat from dissipating up the shaft. The cement is preferably Sauereisen (Pittsburgh, Pa.) No. 350 cement.

The shaft 12 is mounted on a handle 20 containing batteries 29. A less than 24 volt thermal element 22 (available from Ungar, Division of Eldon Industries) carried in the interior of the shaft is in heat transfer contact with the stud 4 which conducts heat to the chisel. The thermal element is connected to the batteries 29 by thermally and electrically insulated conductors 24 extending through the hollow interior of the shaft via an on-off switch 26.

FIGS. 1 and 1a illustrate one embodiment of the thermal chisel 14 which includes a base 28 adapted for heat transfer connection to the stud 4. The end of the base remote from the shaft is necked down to a narrow, elongated heat transfer tip 30 which projects away from the base and then makes a generally right angle bend to a blade end 32 at the working end of the tip.

FIGS. 2 and 2a show an alternate thermal chisel 34 having a base 36 and a heat transfer tip 38 similar in shape to that of chisel tip 30, except that the blade end 40 of the FIG. 2 embodiment has been rotated 90°.

FIGS. 3 and 3a show a further embodiment of a thermal chisel 42 having a base 43 and a heat transfer tip 44 similar to those shown in FIGS. 1 and 2, except that the working end 46 of the tip is pointed. This is a presently preferred configuration for a thermal chisel used in carrying out a pre-molding step of this invention described below.

FIGS. 4 and 4a show an alternate embodiment of a thermal chisel 48 having a base 50 adapted for heat transfer connection to the stud 4. The end of the base 50 is tapered outwardly to form a outwardly converging conical tip to provide a point source of heat at a pointed end 52 of the thermal chisel tip.

FIGS. 5 and 5a illustrate an alternate embodiment of a thermal chisel 54 in which a heat transfer base 56 is narrowed down toward one end as a forward thrust scoop 58.

Referring again to FIGS. 6 and 7, the shafts 12, 12' or 12" can be bent to facilitate use of any of the thermal tips described above. The shaft can be made of a soft ductile metal or hard metal formed as a helix for flexibility, or it can be made of a rigid metal if it is desired to maintain a permanent deformation of the shaft in any desired shape.

FIGS. 8 through 10 illustrate a method for removing bone cement according to this invention. FIG. 8 shows a cross section of a femur 60 after removal of the stem leaving bone cement 62 in an intramedullary canal 64. The instrument 10 is used by inserting it into a cavity previously formed by the stem in the bone cement. The right angle tip of the tool 42 is preferably used to sectionalize a region of the bone cement by pre-molding weakened areas into the bone cement. An impact tool, described below, is then used to remove intact sections of bone cement from between the weakened areas. The weakened areas are preferably formed by contacting the tip of the heated tool with the bone cement to pre-mold indentations into the bone cement (without removing the bone cement from the bone cavity). The temperature of the thermal chisel tip is controllable so that its temperature can be preset to the temperature that rapidly plasticizes the particular bone cement that has been used. Structural deterioration of the bone cement is caused when the bone cement is cooled after thermal contact with the chisel tip. The thermal element 22 of the instrument transfers heat at or above the required plasticizing temperature to the thermal chisel 42 at the end of the shaft 12. The heat transferred to the bone cement from the chisel tip makes the bone cement plastic upon direct contact from the chisel tip. The bone cement has a very low heat coefficient and protects the bone from the thermal effect of the thermal chisel. The cement thermal transfer to a plastic state allows the linear motion of the thermal chisel through the plasticized cement to deform the cement so as to furrow a groove.

The following is one example of a procedure for removing bone cement using principles of this invention. The tip 46 of the thermal chisel 42 is used to thermally mold a circumferential furrow or groove 66 in the bone cement, approximately 25 percent distal down the bone cavity. Using the thermal chisel, preferably four straight longitudinal grooves 68 are then molded in the bone cement to a depth near the bone wall. These grooves are circumferentially spaced approximately 90° apart and extend longitudinally from the circumferential groove 66 to the proximal surface 70 of the bone cement. The bone cement is then allowed to cool. These pre-molding steps form four sectionalized regions of intact bone cement bounded at their perimeter by the weakened areas formed by the furrows. A molded step groove 72 is then made at the proximal end of each of the four sections of bone cement between the longitudinal furrows 68. Each section of bone cement is then removed by placing an impact chisel in the proximal groove formed in each respective section of the bone cement, and then impacting the formed groove with the impact chisel. The step grooves can be molded in any desired shape by selecting the particular shape of the thermal chisel for forming the molded step groove. An impact chisel of the same selected shape is then used for applying impact energy to the section of bone cement. The molded longitudinal furrows weaken the bone cement after the cement rehardens, and the impact applied to each section between the weakened areas removes the entire section of bone cement intact from the wall of the bone. The area of each section of bone cement between the weakened regions is selected so that impact will remove substantially the entire section of bone cement as one intact piece. This procedure makes it possible to remove the bone cement from the bone cavity in large continuous sections which fracture along the interface near the wall of the bone. It is possible to remove the bone cement from the bone cavity without the necessity of using the thermal chisel near the wall of the bone for removing substantial amounts of bone cement from the bone cavity. As a result, the wall of the bone is not used as a means for arresting travel of the thermal chisel through the bone cement, and the resulting dangerous heat transfer from the tip of the thermal chisel to the wall of the bone is substantially avoided.

The above steps of molding circumferential and longitudinal furrows, followed by rehardening of the bone cement and removing the bone cement by direct impact by an impact chisel are repeated until essentially all of the bone cement is removed from the bone cavity.

Figure 11:
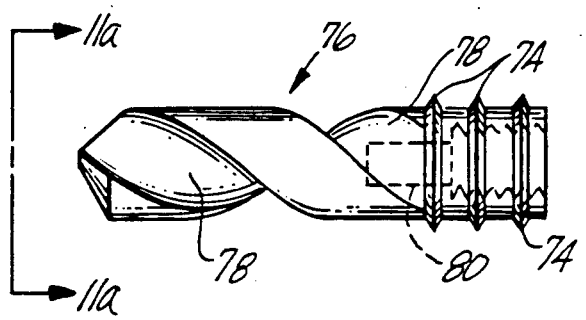
FIG. 11 is a side elevation view of a thermal drill having heat transfer protection rings according to principles of this invention.

The bone cement is removed from the principal area of the bone cavity down to a distal solid cement plug 73. The surgical thermal drill 76 shown in FIGS. 11 and 11a then may be used to remove the distal plug. The drill 76 comprises a drill bit having a helical flute 78 and a thermal element cavity 80. The drill is rotated by hand and is used to drill the distal bone cement plug while the helical flute provides a volume for the plasticized bone cement to collect in during rotation for easy extraction.

Figure 12A:
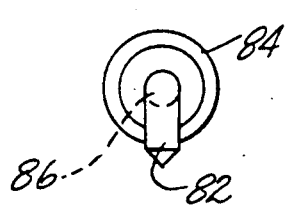
FIG. 12a is an end view taken on line 12a—12a of FIG. 12.
Figure 12:
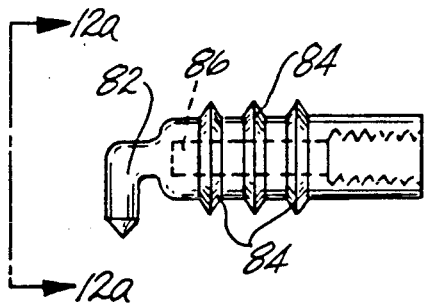
FIG. 12 is a side view of a thermal chisel having heat transfer protection rings according to principles of this invention.

FIGS. 12 and 12a illustrate a surgical thermal chisel comprising a thermal contact edge area 82, which can be in any of the thermal chisel shapes described previously for molding the bone cement. A thermal element is located in a thermal element cavity 86. This instrument further includes a series of longitudinally spaced apart concentric tangential point protection rings 84 which project from the shaft of the tool near its working end. These rings protect the bone from unnecessary heat transfer during accidental contact of the thermal chisel with the bone wall. This is necessary especially while removing the distal cement after the proximal cement has been removed. Any contact between the tool and the wall of the bone is produced by point contact between the protective rings 84 and the bone wall. This greatly reduces the area of heat transfer from the tool to the wall of the bone and thereby prevents damage to the bone wall or to the adjacent tissue.

What is claimed is:

1. A surgical instrument for use in removing bone cement from a bone cavity, comprising:
    an elongated shaft of sufficient length to extend far enough into the bone cavity to mold bone cement forming a wall of the cavity,
    a bone cement removal tool on a working end of the shaft for use in removing bone cement form the wall of the bone cavity,
    a heating element carried by the shaft for transferring heat from the shaft to the bone cement removal tool for heating the tool to a temperature within a range of temperatures sufficient to plasticize the bone cement and thereby deform and weaken it upon direct contact with the heated bone cement removal tool, and
    at least one tangential point protection member affixed to and integral with the shaft and in heat transfer communication with the shaft, the tangential point protection member projecting laterally away from an exterior side wall of the shaft adjacent the bone cement removal tool, the tangential point protection member having an exterior wall surface that converges to an outermost peripheral edge that produces point contact when the member is moved into engagement with the wall of a surrounding bone cavity, so that lateral movement of the heated shaft toward the bone wall will cause the outermost peripheral edge of the tangential point protection member to preferentially contact the bone wall to prevent direct contact of the bone wall with the heated shaft sufficiently to prevent damaging heat transfer from the heated shaft to the wall of the bone.

2. Apparatus according to claim 1 in which the shaft has a great insulating handle at an end opposite from the chisel.

3. Apparatus according to claim 1 including electrical conductors within the shaft extending remotely from the shaft for connection to an electrical power source.

4. Apparatus according to claim 3 in which the elongated shaft and electrical conductors form a common coaxial unit, the outer portion being the elongated shaft and one conductor inside the insulated portion being the other conductor.

5. Apparatus according to claim 1 in which the elongated shaft is bent into a shape conforming to the contour of the medullary canal.

6. Apparatus according to claim 1 in which the elongated shaft has a heat barrier to prevent heat from dissipating up the shaft.

7. Apparatus according to claim 1 in which the bone cement removal tool comprises a bone cement removal chisel having a base and an elongated narrow tip projecting from the base.

8. Apparatus according to claim 7 in which the tip of the chisel provides thermal point contact with the bone cement.

9. Apparatus according to claim 7 in which linear motion of the chisel end in direct contact with the bone cement deforms and furrows a groove in the bone cement.

10. Apparatus according to claim 1 in which the instrument comprises a plurality of said tangential point protection members encircling the shaft at axially spaced apart locations.

11. Apparatus according to claim 10 in which said members have pointed outer edge surfaces.

12. Apparatus according to claim 11 in which said members comprise separate axially spaced apart rings projecting from the shaft of the instrument adjacent the heated tip of the instrument.

13. Apparatus according to claim 1 in which the instrument includes internal and external battery powered heating elements.

14. Apparatus according to claim 1 in which the heating elements are of less than 24 volts.

15. Apparatus according to claim 1 in which the bone cement removal tool comprises a rotary drill and in which the tangential protection member rotates on the shaft with rotation of the drill.

16. Apparatus according to claim 1 in which the heating element heats the bone cement tool to a temperature above at least 400° C.

* * * * *

UNITED STATES PATENT AND TRADEMARK OFFICE
CERTIFICATE OF CORRECTION

PATENT NO. : 5,064,426
DATED : November 12, 1991
INVENTOR(S) : Donald L. Huebsch It is certified that error appears in the above-identified patent and that said Letters Patent is hereby corrected as shown below:

On title page, item

[56] References Cited
U.S. PATENT DOCUMENTS, change "3,919,522  11/1925  Wahl" to
         -- 3,919,522  11/1975  Wahl --.

Column 2, line 31, change "then" to -- than --.
Column 2, line 56, before "the bone" delete "in".
Column 3, line 62, after "penetration" delete "of the".
Column 5, line 50, before "outwardly" change "a" to -- an --.

In the Claims:

Column 7, line 44, change "form" to -- from --.
Column 8, line 11, change "great" to -- heat --.
Column 8, line 59, after "cement" insert -- removal --.

Signed and Sealed this

Twenty-fourth Day of August, 1993

Attest:

BRUCE LEHMAN

*Attesting Officer*     *Commissioner of Patents and Trademarks*